United States Patent [19]

Freedman

[11] 3,931,158
[45] Jan. 6, 1976

[54] CIS AND TRANS-6-SUBSTITUTED-11-AMINOALKYLIDENE-5,6-DIHYDROMORPHANTHRIDINES

[75] Inventor: Jules Freedman, Thiensville, Wis.

[73] Assignee: Richardson-Merrell Inc., Wilton, Conn.

[22] Filed: Dec. 6, 1973

[21] Appl. No.: 422,419

[52] U.S. Cl. ........ 260/240 TC; 260/239 D; 424/244
[51] Int. Cl.$^2$.................................... C07D 223/18
[58] Field of Search.................. 260/240 TC, 239 D

[56] References Cited
UNITED STATES PATENTS
3,699,099  10/1972  Drukker .................. 260/240 TC FOREIGN PATENTS OR APPLICATIONS
1,207,116  9/1970  United Kingdom

OTHER PUBLICATIONS

Kharasch et al., Grignard Reactions of Non-Metallic Substances, Prentice-Hall, N.Y., N.Y., 1954, p. 1204.

Nesmayanov et al., Methods of Elemento-Organic Chemistry, North-Holland Publishing Co., Amsterdam, 1967, p. 608.

*Primary Examiner*—Arthur P. Demers
*Attorney, Agent, or Firm*—Eugene O. Retter; L. Ruth Hattan; George W. Rauchfuss, Jr.

[57] ABSTRACT

Pure cis and trans-6-substituted-11-aminoalkylidene-5,6-dihydromorphanthridines are prepared by treating the morphanthridines unsubstituted in the 6-position with a Grignard reagent in a suitable solvent such as tetrahydrofuran. Among the compounds disclosed are:
cis-2-Chloro-11-(3-dimethylaminopropylidene)-6-phenyl-5,6-dihydromorphanthridine, and
trans-2-Chloro-11-(3-dimethylaminopropylidene)-6-methyl-5,6-dihydromorphanthridine.

The compounds are useful as antihypertensive and anti-Parkinson agents.

3 Claims, No Drawings

CIS AND TRANS-6-SUBSTITUTED-11-AMINOALKYLIDENE-5,6-DIHYDROMORPHANTHRIDINES

BACKGROUND OF THE INVENTION

Methods of preparing 11-(3-dimethylaminopropylidene)-6-methyl-5,6-dihydromorphanthridines are disclosed in Belgian Pat. No. 732,405; Belgian Pat. No. 652,938; and British Pat. No. 1,207,116. The prior art methods possess the disadvantage of producing mixtures of the cis and trans isomer forms which often are undesirable because the pharmacological activity may reside in only one of the isomers.

DETAILED DESCRIPTION

The method of the present invention relates to the preparation of compounds of the formula:

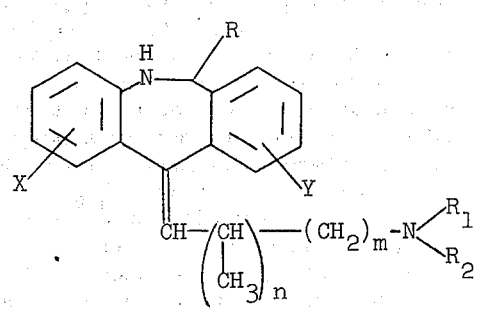

in which n and m are 0 to 3, R is a lower alkyl of 1 to 4 carbon atoms, phenyl or a nuclear substituted phenyl such as p-chlorophenyl and p-methoxyphenyl, $R_1$ and $R_2$ are hydrogen, lower alkyl of 1 to 4 carbon atoms or an aralkyl of 7 to 13 carbon atoms such as benzyl, phenethyl or phenylisopropyl, and X and Y are hydrogen, fluoro, chloro, bromo, trifluormethyl, hydroxy, lower alkyl of 1 to 4 carbon atoms or a lower alkoxy such as methoxy, ethoxy or propoxy.

In the preferred practice of the invention a pure cis or trans isomer of a corresponding 6-unsubstituted morphanthridine is dissolved in a suitable solvent such as tetrahydrofuran and the mixture is allowed to react at room temperature, or, if desired, heated to reflux until the reaction is essentially complete. Normally the reaction proceeds to completion in about four hours. The reaction mixture is then decomposed with ammonium chloride, filtered and the filtrate concentrated to yield the desired product. The process may be illustrated as follows:

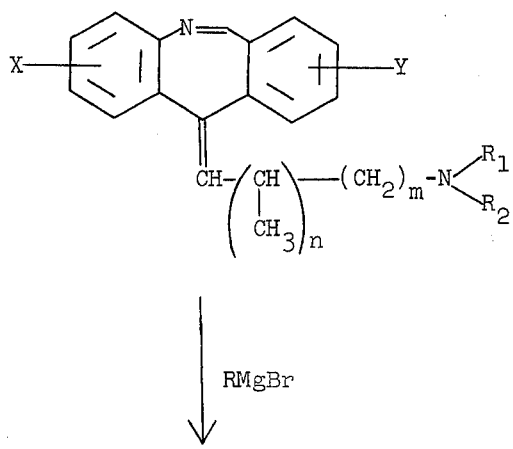

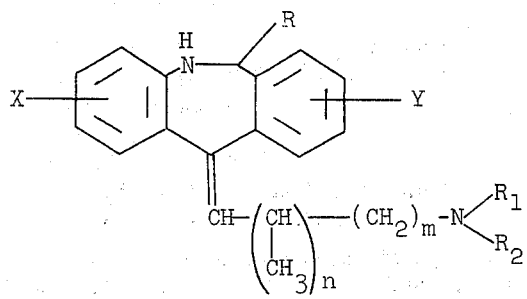

in which all of the symbols are as previously defined.

Representative of the morphanthridines which may be used as starting materials are the following:

cis-2-Chloro-11-(3-dimethylaminopropylidene)morphanthridine, and trans-2-Chloro-11-(3-dimethylaminopropylidene)-morphanthridine.

The unsubstituted morphanthridines are disclosed in U.S. Pat. No. 3,699,099.

Representative of the final compounds that may be prepared by the method of the present invention are:

cis-2-Chloro-11-(3-dimethylaminopropylidene)-6-methyl-5,6-dihydromorphanthridine, cis-2-Chloro-11-(3-dimethylaminopropylidene)-6-phenyl-5,6-dihydromorphanthridine, trans-2-Chloro-11-(3-dimethylaminopropylidene)-6-methyl-5,6-dihydromorphantridine, and tran-2-Chloro-11-(3-dimethylaminopropylidene)-6-phenyl-5,6-dihydromorphanthridine.

The methyl substituted compounds are disclosed in Belgian Pat. No. 652,938 and U.S. Pat. No. 3,692,906. They are antihypertensive agents and anti-tremor agents, as well as intermediates in the preparation of the corresponding morphanthridines. When either the cis or the trans form of many of the compounds possess activity, whereas the corresponding isomer does not, it is extremely important that the isomers be obtained in as pure a form as possible. Prior to the development of the method of the present invention, it was extremely difficult to obtain the pure isomers without going through extensive separation procedures after the preparation of the final compounds.

The practice of the present invention is further illustrated by the following examples:

EXAMPLE 1 trans-2-Chloro-11-(3-dimethylaminopropylidene)-6-phenyl-5,6-dihydromorphanthridine A Grignard reagent is prepared from 11.0 g. (0.07 M) of bromobenzene, 1.70 g. (0.07 M) of magnesium and 70 ml. of tetrahydrofuran. A solution of trans-2-chloro-11-(3-dimethylaminopropylidene)morphanthridine (10.9 g., 0.035 M) in 100 ml. of tetrahydrofuran is added and the mixture stirred at room temperature for 18 hours, cooled in ice and decomposed with 17 ml. of saturated ammonium chloride. The solids are filtered and the residue is taken up in ether. Addition of dilute hydrochloric acid precipitates a viscous, water insoluble oil. This is dissolved in methanol and treated with 10% sodium hydroxide. The oil is taken up in ether and the solution washed with saturated sodium chloride and dried over potassium carbonate. The residue is distilled in a Kugelrohr apparatus to give 11.5 g. of trans-2- chloro-11-(3-dimethylaminopropylidene)-6-phenyl-5,6-dihydromorphanthridine as a yellow-brown glass. Redistillation at 140°–150°/0.02 mm. gives 11.2 g. of the product.

Anal. Calcd. for $C_{25}H_{25}ClN_2$: C, 77.21; H, 6.48; Cl, 9.11; N, 7.20. Found: C, 77.14; H, 6.62; Cl, 9.15; N, 7.02.

EXAMPLE 2 cis-2-Chloro-11-(3-dimethylaminopropylidene)-6-methyl-5,6-dihydromorphanthridine To a Grignard reagent prepared from 28.4 g. (0.2 M) of methyl iodide, 5.4 g. (0.22 M) magnesium and 200 ml. of ether, a solution of 31.1 g. (0.1 M) of cis-2-chloro-11-(3-dimethylaminopropylidene)morphanthridine in 300 ml. of ether is added in a slow stream. After 3.5 hours, the mixture is cooled in ice and decomposed with 20 ml. of saturated ammonium chloride solution. The solids are filtered and leached with chloroform. The combined filtrates are dried over potassium carbonate and concentrated. The residue is recrystallized from 175 ml. of ethanol to give 24.3 g. of cis-2-chloro-11-(3-dimethylaminopropylidene)-6-methyl-5,6-dihydromorphanthridine as a light yellow solid, m.p. 142°–144°. A 4.3 g. portion recrystallized from 25 ml. of ethanol gives 3.5 g. of the product, m.p. 143°–146°.

Anal. Calcd. for $C_{20}H_{23}ClN_2$: C, 73.49; H, 7.09; Cl, 10.85; N, 8.57. Found: C, 73.35; H, 7.14; Cl, 10.94; N, 8.47.

EXAMPLE 3 trans-2-Chloro-11-(3-dimethylaminopropylidene-6-methyl-5,6-dihydromorphanthridine The Grignard reagent is prepared from 19.9 g. (0.14 M) of methyl iodide, 3.40 g. (0.14 M) of magnesium and 150 ml. of dry ether. To this a solution of 21.8 g. (0.07 M) of trans-2-chloro-11-(3-dimethylaminopropylidene)morphanthridine in 200 ml. of ether is added, the mixture is stirred for four hours, cooled in ice and decomposed with 11 ml. of saturated ammonium chloride. The solids are filtered and the filtrate extracted with dilute hydrochloric acid. The solids are stirred with chloroform and the latter evaporated to give 24.8 g. of oil. Trituration with n-heptane gives a high melting solid. The n-heptane is then extracted with 1N acetic acid and the extracts made basic. The oil which forms is extracted into ether, the extracts dried and the solvent removed. Kugelrohr distillation at 130°–135°/0.2 mm. gives 13.0 g. of trans-2-chloro-11-(3-dimethylaminopropylidene)-6-methyl-5,6-dihydromorphanthridine as a yellow oil.

Anal. Calcd. for $C_{20}H_{23}ClN_2$: C, 73.49; H, 7.09; Cl, 10.85; N, 8.57. Found: C, 73.40; H, 7.18; Cl, 10.70; N, 8.50.

EXAMPLE 4 cis-2-Chloro-11-(3-dimethylaminopropylidene)-6-phenyl-5,6-dihydromorphanthridine The Grignard reagent is prepared from 20.4 g. (0.13 M) of bromobenzene, 3.16 g. (0.13 M) of magnesium and 130 ml. of tetrahydrofuran. To this a solution of 20.2 g. (0.065 M) of cis-2-chloro-11-(3-dimethylaminopropylidene)morphanthridine in tetrahydrofuran is added in a slow stream. The solution is stirred at room temperature overnight and then refluxed for 7 hours. After cooling, the mixture is decomposed with 15 ml. of saturated ammonium chloride. The solids are filtered and leached with chloroform. The combined filtrates are dried over potassium carbonate and the solvent removed. Recrystallization from 200 ml. of acetonitrile gives 19.9 g. of cis-2-chloro-11-(3-dimethylaminopropylidene-6-phenyl-5,6-dihydromorphanthridine, m.p. 141°–144°. A 5.0 g. sample recrystallized from 50 ml. of acetonitrile gives 4.6 g. of the product, m.p. 144°–146°.

Anal. Calcd. for $C_{25}H_{25}ClN_2$: C, 77.21; H, Cl, 9.11; N, 7.20. Found: C, 77.06; H, 6.50; Cl, 9.21; N, 7.17.

I claim:

1. cis-2-Chloro-11-(3-dimethylaminopropylidene)-6-phenyl-5,6-dihydromorphanthridine.
2. trans-2-Chloro-11-(3-dimethylaminopropylidene)-6-phenyl-5,6-dihydromorphanthridine.
3. The compound 2-chloro-11-(3-dimethylaminopropylidene)-6-phenyl-5,6-dihydromorphanthridine.

* * * * *

UNITED STATES PATENT OFFICE
CERTIFICATE OF CORRECTION

PATENT NO. : 3,931,158
DATED : January 6, 1976
INVENTOR(S) : Jules Freedman

It is certified that error appears in the above-identified patent and that said Letters Patent are hereby corrected as shown below:

Column 2, line 34, "dihydromorphantridine" should read "dihydromorphanthridine"; line 35, "tran-2-" should read "trans-2-". Column 3, line 33, "3-dimethylaminopropylidene" should read "3-dimethylaminopropylidene)".
Column 4, line 35, "H,     " should read "H, 6.48;"

Signed and Sealed this fourth Day of May 1976

[SEAL]

Attest:

RUTH C. MASON
Attesting Officer

C. MARSHALL DANN
Commissioner of Patents and Trademarks